(12) United States Patent
Bos et al.

(10) Patent No.: US 12,379,156 B2
(45) Date of Patent: Aug. 5, 2025

(54) SUPERSONIC DEHYDRATION AND DISINFECTION SYSTEM AND METHOD

(71) Applicant: Arie Cornelis Bos, Rotterdam (NL)

(72) Inventors: Arie Cornelis Bos, Rotterdam (NL); Jaap Wind, Boxmeer (NL)

(73) Assignee: Arie Bos, Rotterdam (NL)

( * ) Notice: Subject to any disclaimer, the term of this patent is extended or adjusted under 35 U.S.C. 154(b) by 777 days.

(21) Appl. No.: 17/637,717

(22) PCT Filed: Aug. 28, 2020

(86) PCT No.: PCT/IB2020/058066
§ 371 (c)(1),
(2) Date: Feb. 23, 2022

(87) PCT Pub. No.: WO2021/038521
PCT Pub. Date: Mar. 4, 2021

(65) Prior Publication Data
US 2022/0282915 A1 Sep. 8, 2022

Related U.S. Application Data

(60) Provisional application No. 62/893,454, filed on Aug. 29, 2019.

(51) Int. Cl.
*F26B 5/04* (2006.01)
*A61L 2/025* (2006.01)
*F26B 15/10* (2006.01)

(52) U.S. Cl.
CPC .............. *F26B 5/041* (2013.01); *A61L 2/025* (2013.01); *F26B 15/10* (2013.01); *A61L 2202/122* (2013.01)

(58) Field of Classification Search
CPC .......... F26B 5/041; F26B 15/10; A61L 2/025; A61L 2202/122
(Continued)

(56) References Cited

U.S. PATENT DOCUMENTS 2,887,390 A  5/1959  Coulter et al.
2,921,646 A * 1/1960  Poole ........................ B04C 3/00
                                                             55/327
(Continued)

FOREIGN PATENT DOCUMENTS

CA     3149021 A1 *  3/2021  ............... A23B 4/03
RU     2129397 C1     4/1999
WO   WO-2021038521 A2 * 3/2021 ............... A23B 4/03

OTHER PUBLICATIONS

Communication and Supplemental European search report for corresponding European application No. 20858829.3, dated Sep. 15, 2023.
(Continued)

*Primary Examiner* — Stephen M Gravini
(74) *Attorney, Agent, or Firm* — Notaro, Michalos & Zaccaria P.C.

(57) ABSTRACT

The partial or full dehydration of organic or inorganic matter containing water by induction of matter into a vacuum and processing matter through a specially designed acceleration channel is disclosed. The inducted matter accelerates in air from zero speed to sub-sonic speed to reach supersonic speed. As the material transitions the sound barrier, it is subject to acoustic shock waves and an instant negative pressure drop occurs. The sound waves disintegrate, disinfect the material and extract part or all moisture from any organic or inorganic material.

10 Claims, 7 Drawing Sheets

(58) Field of Classification Search
USPC .......................................................... 34/360
See application file for complete search history.

(56) References Cited

U.S. PATENT DOCUMENTS

| | | | | |
|---|---|---|---|---|
| 3,941,609 | A * | 3/1976 | Stern | ........................ C09C 1/625 |
| | | | | 106/14.44 |
| 4,380,127 | A | 4/1983 | Roberts | |
| 4,833,793 | A * | 5/1989 | White | ................. F26B 17/1433 |
| | | | | 34/178 |
| 6,158,145 | A * | 12/2000 | Landon | ................. F26B 17/107 |
| | | | | 34/364 |
| 6,978,953 | B2 | 12/2005 | Graham | |
| 7,040,557 | B2 | 5/2006 | Graham | |
| 7,059,550 | B2 | 6/2006 | Graham | |
| 7,380,348 | B2 * | 6/2008 | Seebach | ................ F26B 17/105 |
| | | | | 34/594 |
| 7,429,008 | B2 | 9/2008 | Graham | |
| 7,909,577 | B2 | 3/2011 | Graham et al. | |
| 8,057,739 | B2 | 11/2011 | Case | |
| 9,309,477 | B2 * | 4/2016 | Foss-Smith | ............... F26B 5/02 |
| 9,347,705 | B2 * | 5/2016 | Crosset | ................ F26B 25/003 |
| 9,671,164 | B2 * | 6/2017 | Forsyth | ................... F26B 3/084 |
| 10,240,866 | B2 * | 3/2019 | Palic | ....................... F26B 5/044 |
| 10,900,714 | B2 * | 1/2021 | Lawie | ..................... F26B 21/10 |
| 10,955,189 | B2 * | 3/2021 | Saribal | ................... F26B 21/10 |
| 2006/0051236 | A1 | 3/2006 | Case | |
| 2007/0014684 | A1 | 1/2007 | Case | |
| 2007/0240328 | A1 | 10/2007 | Moles | |
| 2011/0272502 | A1 | 11/2011 | New | |
| 2013/0081934 | A1 | 4/2013 | New | |
| 2013/0212899 | A1 | 8/2013 | Haimer et al. | |
| 2022/0282915 | A1 * | 9/2022 | Bos | ......................... A23B 2/90 |

OTHER PUBLICATIONS

International Search Report and Written Opinion for corresponding PCT application No. PCT/IB2020/058066, mailed Feb. 17, 2021.
Communication in corresponding EP 20858829.3 enclosing third party observations, dated Oct. 21, 2024.
Communication in corresponding EP 20858829.3 enclosing third party observations, dated Oct. 28, 2024.
Official Action for corresponding EP 20858829.3, dated Jan. 15, 2025.

* cited by examiner

SUPERSONIC DEHYDRATION AND DISINFECTION SYSTEM AND METHOD

FIELD OF THE DISCLOSURE

The present disclosure relates generally to systems and methods for drying and disinfecting organic materials.

BACKGROUND

Drying Organic Materials

In agriculture, crops and plants are harvested after they have fully grown and produced crop or produce. For most agricultural products, except for greenhouse operations, harvesting is bound to certain seasons throughout the year. The harvested product always contains water. Some products, like tomatoes, consist of a large percentage of water, while others, like corn, contain much less.

All products require transportation from the farm. Transportation and storage represent a significant additional cost factor for growers, distributors and, indirectly, for consumers. These costs may be substantially reduced by drying certain produce before transportation. Crop drying also extends the useable shelf life and/or storage life of the produce.

A substantial percentage of all agricultural products is used in bulk the food industry instead of being directly consumed. Sometimes lesser quality products are selected for this purpose, and packaging and transportation of bulk products requires less care than products intended for direct consumer sales.

With certain products, e.g. tomatoes, trucks can be fully loaded to transport the tomatoes to a tomato-processing company where the produce is used as an ingredient in other food products such as pizza, soup, or ketchup. Tomatoes contain 80% water and bell peppers contain 80% air. Transporting such produce is inefficient as mostly water or air is being transported. At the processing site the uncut, wet product requires considerable storage space before it can be processed. Special conditions such as refrigeration and related costs to avoid decomposition and molding (mildew) of the product at the processing site may be required before the material can be processed.

Other products, like hemp, hops, or grains, cannot be processed directly. They first need to dry. Sometimes this happens on the land with all related risks of weather, insect, bird or vermin damage, mold, mildew, and rot in the product. For example, hemp tops, grown for the production of medicinal CBD oils, must be dried within 48 hours after harvesting to prevent mold.

Furthermore, the longer harvested produce waits before being dried and processed, the more its quality deteriorates.

In other situations, the produce is transported in wet and fresh condition and is dried using industrial processes. For example, hops to produce beer, or hemp buds to produce CBD oils. In order to dehydrate large quantities of hops, breweries have their own hop-driers. These are large machines and batch operated. The machines dry hops using high temperatures, fossil fuels and require several hours to dry the hops. This intensive process is not suitable for every product. For example, for hemp this process is not optimal. The high temperature and possible fumes can damage or destroy the medicinal CBD oil, which is extracted from the buds.

Many agricultural products that need drying, lose a substantial part of the nutrients or the food quality (vitamins, fiber strength) due to the high temperature to which they are exposed during the drying process.

Most agricultural products grown on vines, bushes or in orchards trees leave a considerable waste biomass after harvest of the grape, berries, or fruit. The waste biomass includes trimmings, stalks, leaves and root mass. This material then needs to be removed and is treated as agricultural waste. It must either be transported to an approved incineration facility or landfill or left in the open field to naturally decompose. It cannot be re-used immediately or sold as bio-organic fertilizer.

This plant waste can become a very heavy and voluminous mass. For example, from large greenhouses. For example, for tomato crops. Many have several hundred acres under glass. The seasonal waste is not edible by livestock and has no purpose, except being used as biofuel after it has been dried. The waste material can no longer be burned in the open air due to pollution controls. It is transported to specialized incineration facilities. It is expensive to transport raw, wet, bulky waste biomass. A solution is "on site" drying to reduce weight, volume, and transportation costs.

Most processes for drying organic material use fossil fuel to heat up material to be dried. The material is spread out over wide and long (roller) beds, and is transported slowly over a heated area, during which time the material dehydrates. These installations are normally large and capital intensive and consume a large amount of energy. Because of the long time the organic material is exposed to high temperatures, the quality of ingredients may be compromised.

Other drying installations will only dry extremely wet (>90% moisture) materials like hog-manure using centrifuges. The maximum reduction of moisture in this method is approximately 50%.

Treating Waste

In some countries, manure from livestock and litter from poultry farms is a large problem. Chicken litter contains high concentrations of nitrates or ammonia. In many countries, it is not allowed to use this manure as fertilizer as it will gradually destroy the capacity of soils to grow new crops. Specialized companies empty the wet manure pits and/or transport the chicken litter. Animal manure, for example pig manure, can contain more than 90% water. This is converted on-site into biogas. This requires substantial investment in storage tanks and many biogas facilities are closing because natural gas is less expensive. Alternately, the liquid manure is transported to locations where it is dried, separated, and processed. This is a very costly obligation for the farmers and imposes a heavy regulatory burden on farmers, processing companies and regulators.

Worldwide, household waste is a mixed combination of non-organic (mainly paper, glass, and plastics), and organic (food waste) materials. The organic materials contain high levels of moisture. Drying and compacting these waste products prior to disposal in landfill, or being able to recycle them, is an ongoing environmental priority.

Slaughterhouse waste can consist of many animal parts that are not used in the production of food. Examples are chicken hearts and liver, bones, blood and non-edible organs from cattle and pigs. These, and other parts, go to specialized companies who can extract the proteins of all this waste material for the purpose of food supplements, pet-food, and other products. A large proportion of these waste animal parts, in terms of both weight and volume, is comprised of water that is not useful to the companies that take these waste parts. Transportation of the waste animal parts in their original form, including the water, is therefore inefficient.

In some agricultural industries, large volumes of water are needed as irrigation water to produce crops (e.g. tomatoes). The roots, stems, stalks, and leaves are long, heavy and contain up to 85% water. The plant can reach a length of 14-15 meters. The waste plants are cut and disposed of. For large tomato producers, this means millions of liters of water are lost after each growth cycle. If these waste plants are shredded and dried, the water may be extracted and fed back into the irrigation system of a greenhouse. Weight and volume of the dried biomass is also reduced. This, in turn, reduces disposal handling and transportation costs.

In some food industries, large amounts of partially prepared foods are ultimately not used and can become difficult to remove, process and store. As an example, large industrial bakeries have fixed daily supply contracts with large retail client including supermarket chains. The chain grocery stores process their daily sales results for the day and adjust purchases of incoming products for the next morning. This can mean that a bakery, having a fixed order contract, for example, for 300,000 loaves of bread a day, is notified at 9 p.m. that 50,000 of them are canceled. However, the dough is already prepared and must be destroyed. That material is very sticky, and a large portion of it is comprised of water. The costs of getting the material out of the machine and packing and storing it as waste material are high. A large part of this cost is due to the high proportion of water, both in terms of volume and weight, contained in the waste product. This water makes the product much heavier and more cumbersome to handle.

With growing environmental awareness and responsibility, large waste processing companies have been established in the last 10 years. One area of their activities is the processing of household organic waste (fruit, vegetables, garden, called GFT). In many countries GFT must be disposed of separately from plastic, glass paper and other materials. GFT is processed in bio-digestors, and exits as a heavy, smelly sludge. It still contains approximately 55% water. It then is dried in large fossil-fuel based drying installations using expensive natural gas or propane. It is then mixed with peat and sold in garden centers as fertilizer.

Companies exists in Europe to process used infant and adult diapers. These consist of a combination of high-quality plastics and man-made absorbent material. After use, they are disposed of separately by consumers, for example, in the Netherlands, Germany and Belgium. The absorbent fibers cannot be separated from the plastic. The diapers are rinsed and then dried, melted, shredded, and recycled into low-grade products, such as road signs. If the absorbent material can be dried and separated from the plastic, the plastic could then be used to produce higher value recycled products.

In general household waste, plastic bags and packaging are a major problem to separate and process as waste. Because all waste contains fluids and fats (example: yoghurt, butter, oils, left over drinks, rotting fruits and vegetables and many more), it is very hard to recycle the plastic elements in it. If this wet waste could be easily dried, it would be possible to separate the plastics from the organic materials, and the plastics could be recycled.

Worldwide, civil maintenance service companies clean out sewage systems of "human manure". This matter contains only a small percentage of solid materials, the remainder is moisture. To be permitted to transport "human manure" in accordance with regulations in Europe (and elsewhere), it must be dry and free of bacteria. There are relatively easy ways to reduce the moisture level to 30%, but further reduction is difficult and expensive. There appear to be no known inexpensive or efficient ways to dry the manure matter on site such that transport is allowed. If the material would be completely dry, free of bacteria and smell, transportation and disposal would be simpler, and less expensive.

Pulverizing Materials

Zeolite is abundantly available worldwide. It is a light, soft rock. It is used as a soil conditioner on agriculture, in animal feedstocks and in water treatment. In certain deposits of zeolite flakes of gold can be found. To separate the gold traces from the zeolite is difficult. Grinding and applications of toxic chemicals is required. Drying and pulverizing the zeolite would facilitate gold extraction.

Another recently discovered application for zeolite is its fire-extinguishing capacity when used in powdered form. This powder could replace water, dispatched from firefighting aircraft. It weighs much less than water and has equal or better extinguishing capabilities. Zeolite is also beneficial to soils. It can replace environmentally harmful fire suppressants currently in use.

Some volcanic rock contains extraordinary combinations of minerals. It is known that these minerals, once extracted and dissolved in water, can have positive impact on the health of human beings and animals, and can increase crop yields. Currently, to convert massive 1-ton pieces of volcanic rock into a powder from which minerals can be dissolved into water, takes 9 steps, of which the last 5 steps are the most expensive. These last 5 steps bring the material from approx. ¾ of an inch to fine powder, which is required before minerals can be extracted and dissolved in water.

In the food industry, nuts are used in many products. Nuts are mainly used in pressed (oil) or pulverized form as an ingredient for food products, the process to dry and pulverize the nuts is costly and time consuming.

All the foregoing examples illustrate scenarios in which the ability to dry moisture-bearing material, or to pulverize organic and non-organic materials, would be highly beneficial. Many existing technologies and equipment for drying use thermal processes (essentially hot air ovens) and fossils fuels to slowly dehydrate the target products. In certain situations, and with certain materials (for example, hemp-buds), the time that this process takes, and the temperature used to dry the material adversely impact the quality of the final product.

Disinfection and Eradication

In other situations, bacteria must be eradicated from manure, sludge, waste materials and infected crops. This is a difficult process and is based mainly upon the use of fossil fuels to eradicate bacteria, fungi, spores, and mildew.

Also, the human manure referred to above may be used as crop fertilizer, but only if it is free of bacteria. Currently, there are no known ways to guarantee that such manure is bacteria free. If this could be done, human manure could be used as fertilizer.

In other situations, airborne bacteria or viruses need to be eradicated from airstreams. For example, in buildings like airports, factories, hospitals, educational facilities, government buildings, theaters, convention centers, hotels, casinos and large greenhouse complexes, large volumes of air need to be cleaned and disinfected, or kept as bacteria- and virus-free as possible. There are several methods to eradicate air-borne pathogens. Some of these technologies work instantly but with low volume or capacity, others work with a high capacity but work slowly and on a continuous basis. However, there is a global need for exceptionally large volumes of air to be disinfected both constantly and instantaneously.

Combinations of the Above

Severe virus outbreaks, whether local or global, cause tremendous problems in many sectors of society and industry. In particular, the animal industry and the food industry face enormous problems with the growth and the slaughtering of animals. In some cases, whole animal farms must be closed, and all animals are destroyed in the event infections are found, even when only a single animal is detected as the carrier of a disease. There is no good way to dispose of these animals except preventive clearance by euthanasia and incinerating or burying the animals. They cannot go to a slaughterhouse.

In similar situations, slaughterhouses themselves can be a source of infection and its spread. Continuously cold working environments may be bad for bacteria but are actually good for viruses. When slaughterhouses are closed, as in current times, even temporarily, thousands of animals remain at farms where they must be fed or euthanized.

World-wide, large amounts of meat is currently produced but not used. Special facilities exist where this meat is being destroyed. This is to prevent bacterial spread when the meat decomposes. Caution in handling the material is of great importance. When meat rots, maggots and other protein-rich lifeforms transition themselves from leftover meat into new form of life. All these materials, whether alive or dead, are extremely protein rich, and could be a perfect base for animal food provided it is quickly processed and efficiently and made bacteria-free.

In similar situations, there is a need for animals to get mineral and protein rich food, combined with the right fibers to stimulate healthy digestion. When animals are fed nutritious food, the risk of developing infections, and therefore becoming a cost item to the farmer instead of a profit item, is greatly reduced. This situation can be achieved by mixing proteins, fibers, and carbohydrates in the right way, and in the right composition. If such nutritious food can be produced in a cost-effective manner, the need and cost for medicines, antibiotics, additional nutrients, and vitamins for animals can be substantially reduced.

SUMMARY OF THE INVENTION

The present disclosure provides an apparatus for dehydrating or disinfecting material, comprising: an acceleration channel having an inlet for receiving an air stream and material to be dehydrated, an outlet for discharging said air stream and dehydrated, disinfected material, and a constriction positioned between the inlet and the outlet; an air mover in communication with the acceleration channel for moving an air stream and material to be dehydrated through the acceleration channel such that the velocity of the air stream and material moving through the constriction is equal to or greater than the speed of sound; and a cyclone in communication with the outlet of the acceleration channel for receiving said discharged air stream and dehydrated, disinfected material, and separating said dehydrated, disinfected material from said air stream.

In some embodiments, the constriction is positioned at least 400 millimeters from the inlet of the acceleration channel.

In some embodiments, the constriction comprises: an inclination section, along the length of which the diameter of the acceleration channel decreases; a widening section, along the length of which the diameter of the acceleration channel increases; and a throat, located at a point between the inclination section and the widening section where the diameter of the acceleration channel is smallest.

In some embodiments, the length of the inclination section is within the range of 100 millimeters and 400 millimeters.

In some embodiments, the length of the widening section is within the range of 60 millimeters and 120 millimeters.

In some embodiments, the ratio of the diameter of the acceleration channel at the throat, to the maximum diameter of the acceleration channel is within the range of 1:2.5 to 1:10.

In some embodiments, the acceleration channel has an interior diameter of about 160 millimeters at all points outside the constriction.

In some embodiments, an intake of the air mover is in communication with the outlet of the acceleration channel, and the cyclone is in communication with an outlet of the air mover.

In some embodiments, the air mover is a turbine capable of generating under pressure in the range of −290 millibar to −390 millibar, and airflow capacity in the range of 1.5 $m^3$ per second to 1.66 $m^3$ per second.

In some embodiments, the apparatus further comprises an air pressure sensor in communication with the acceleration channel, for measuring air pressure within the channel.

The present disclosure also provides a method of dehydrating, the method comprising the steps of: directing an air stream and material to be dehydrated through an acceleration channel having an inlet for receiving the air stream and material to be dehydrated, an outlet for discharging the air stream and material, and a constriction positioned between the inlet and the outlet, the air stream and material to be dehydrated having a velocity through the constriction greater than or equal to the speed of sound; and directing the discharged air stream containing dehydrated particulate material in a helical trajectory, causing the dehydrated particulate material and air stream to separate.

In some embodiments, the air stream and material to be dehydrated are directed through the acceleration channel by an air mover having an air mover inlet in communication with the outlet of the acceleration channel, the air mover drawing the air stream and material to be dehydrated in the inlet, through the acceleration channel, out the outlet and into the air mover inlet.

In some embodiments the method further comprises monitoring the velocity of the air stream through the constriction by measuring the air pressure and determining air stream velocity based on the measured air pressure, the volume of air moved per second by the air mover at the measured air pressure, and the area of the constriction.

In some embodiments, the method further comprises adjusting the velocity of the air stream to ensure the velocity through the constriction remains above the speed of sound.

In some embodiments, the discharged air stream containing dehydrated particulate material is directed into a cyclone in which the air stream and dehydrated particulate material move in a helical trajectory.

The present disclosure also provides a method of recovering moisture from material having a moisture content, the method comprising the steps of: directing an air stream and material to be dehydrated through an acceleration channel having an inlet for receiving the air stream and material to be dehydrated, an outlet for discharging the air stream and material, and a constriction positioned between the inlet and the outlet, the air stream and material to be dehydrated having a velocity through the constriction greater than or equal to the speed of sound; directing the discharged air stream containing dehydrated particulate material in a helical trajectory, causing the dehydrated particulate material and air stream to separate; and directing the air stream into a moisture collector for recovering moisture from the air stream.

In some embodiments, the moisture collector is a condenser or an oil filter.

In some embodiments, the air stream and material to be dehydrated are directed through the acceleration channel by an air mover having an air mover inlet in communication with the outlet of the acceleration channel, the air mover drawing the air stream and material to be dehydrated in the inlet, through the acceleration channel, out the outlet and into the air mover inlet.

In some embodiments, the method further comprises monitoring the velocity of the air stream through the constriction by measuring the air pressure and determining air stream velocity based on the measured air pressure, the volume of air moved per second by the air mover at the measured air pressure, and the area of the constriction.

In some embodiments, the method further comprises adjusting the velocity of the air stream in response to the observed velocity of the air stream through the constriction, to ensure the velocity through the constriction remains above the speed of sound.

In some embodiments, the discharged air stream containing dehydrated particulate material is directed into a cyclone in which the air stream and dehydrated particulate material move in a helical trajectory.

The present disclosure also provides a method of disinfecting material, the method comprising directing an air stream and material to be disinfected through an acceleration channel having an inlet for receiving the air stream and material to be disinfected, an outlet for discharging the air stream and material, and a constriction positioned between the inlet and the outlet, the air stream and material to be disinfected having a velocity through the constriction greater than or equal to the speed of sound.

In some embodiments, the air stream and material to be disinfected are directed through the acceleration channel by an air mover having an air mover inlet in communication with the outlet of the acceleration channel, the air mover drawing the air stream and material to be dehydrated in the inlet, through the acceleration channel, out the outlet and into the air mover inlet.

In some embodiments the method further comprises monitoring the velocity of the air stream through the constriction by measuring the air pressure and determining air stream velocity based on the measured air pressure, the volume of air moved per second by the air mover at the measured air pressure, and the area of the constriction.

In some embodiments the method further comprises adjusting the velocity of the air stream to ensure the velocity through the constriction remains above the speed of sound.

In some embodiments, the discharged air stream containing disinfected particulate material is directed into a cyclone in which the air stream and disinfected particulate material move in a helical trajectory and are separated.

In some embodiments, the material to be disinfected is itself a mass of air.

BRIEF DESCRIPTION OF THE DRAWINGS

The present disclosure is better understood having regard to the drawings in which:

FIGS. 1A and 1B are graphs showing temperature, pressure, and velocity of air flow through an acceleration channel of an embodiment of the present disclosure. Temperature, pressure and velocity are shown as a function of position in the acceleration channel, in the case where velocity remains below the speed of sound (FIG. 1A) and in the case where velocity exceeds the speed of sound (FIG. 1B);

FIG. 2 depicts the air velocity at different points within an acceleration chamber, during operation according to the present disclosure;

FIG. 3 depicts an embodiment of the acceleration channel of the present disclosure, and the acoustic shockwaves that form in the area of the constriction in the acceleration channel;

FIG. 4 is a cross section of an acceleration channel according to an embodiment of the present disclosure;

FIG. 5 is a graphical representation of pressure drops occurring through an embodiment of an SSD system in accordance with the present disclosure;

FIG. 6 is a graph showing certain specific characteristics of a turbine used in an embodiment of the present disclosure;

FIG. 7 is a schematic view of an embodiment of the present disclosure;

FIG. 8 is a further schematic view of the embodiment shown in FIG. 7;

FIG. 9 is a schematic view of another embodiment of the present disclosure;

FIG. 10 is a further schematic view of the embodiment shown in FIG. 9; and FIGS. 11, 12 13 and 14 are schematic views of other embodiments of the present disclosure.

DETAILED DESCRIPTION

Supersonic Dehydration (SSD) is a physical process caused by induction of target material, such as organic material, into a powerful vacuum and processing through an acceleration channel. The inducted material accelerates in air from zero speed to sub-sonic speed and then passes through transonic speed to reach supersonic speed (342 meters/second and higher). The inducted matter can be any crop such as hemp, corn, grains, seeds, fruits and nuts and plant wastes such as greenhouse plant wastes, vineyard and orchard cuttings, garden wastes, household, or industrial organic waste. As the material transitions the sound barrier it is subject to acoustic shock waves and an instant pressure drop and temperature drop occurs. The shock waves disintegrate the material and separates water and other liquids from the material and/or pulverizes solid materials such as rocks, glass, and various minerals. No heat or other form of energy is required in the process. No fossil fuels are used. No chemicals or processing agents are used.

It has also been found that small pathogens such as bacteria and viruses are not able to withstand the acoustic shock wave that disintegrates the material. In testing, a sample of animal waste inoculated with *Enterococcus faecalis* bacteria was treated using the SSD process. After two passes through the SSD process, meaning the sample was transitioned the sound barrier and was subject to acoustic shock waves twice, a reduction in the amount of live *Enterococcus faecalis* in the sample was observed. Specifically, the amount of live *Enterococcus faecalis* was observed to decrease by 3.5 $\log_{10}$ units, or by a factor of approximately 5,000.

The powerful vacuum that accelerates material to supersonic speed can be created using aero dynamic technology to move air through the acceleration channel. Turbines are industrial products which propel large volumes of air at high velocity. They exist in many different varieties, like jet engines or industrial fans. Acceleration channel tubes, also known as venturi tubes, are also known products comprising a tube having a constriction wherein the diameter of the tube at the constriction is decreased relative to other sections of the tube, and is at a minimum at a point known as the "throat". Air or other fluids moving through such acceleration channel tubes are subject to the well-known venturi effect, wherein velocity increases, and pressure decreases as it passes through the constriction. The air (or other fluid) is moved at a velocity such that, when the air stream moves through the constriction, it accelerates to the speed of sound at a certain point in the process.

Cyclones are industrial products designed to separate particles from air or gasses, or to separate liquids with different specific weights. The principle of a cyclone is that high speed air streams containing solid particulate matter is directed into the tangent-aligned input conduit of a vertically positioned cylinder. The air and particles spin at high speed in a "tornado" vortex, having a helical trajectory. The particles of solid material drop in a downwards direction through gravitational effect and air and extracted moisture vapor exit in an upwards direction through a centrally positioned acceleration channel.

In the processing of the target material, the moisture in the material may be fully extracted from the organic material, in which situation the material will exit the cyclone in fully dried form.

In the processing of the target material, the moisture in the material may also be partially extracted from the organic material, in which situation the material will exit the cyclone as partially dried material.

In case material is not completely dried in a single pass or cycle, it can be recycled into the main material stream so the input material's moisture can be controlled in order to reach the optimal moisture level in the outgoing material.

Alternatively, two SSD systems may be placed in cascade in one single enclosure to process material twice (or more) to reach complete drying. In many situations, a small percentage of residual moisture is desirable for transportation or to substantially reduce the process of molding or rotting of organic materials.

Alternatively, two or more SSD systems may be placed in parallel to increase the processing capacity in one single enclosure.

The present disclosure is described having regard to several embodiments with reference to the Figures. While these embodiments are described generally in the context of dehydration and the applications of processing biomass, the scope of the present disclosure is not intended to be limited to the context of these applications. The present disclosure may be used in other applications and in other fields, such as pulverizing materials, disinfecting materials or air and cleaning water, effluent and other liquids, and for desalinating water.

Although the term "system" is used in this disclosure, it is not used in a limiting manner. Rather, a dehydration "system" generally includes methods, processes, structures, equipment, etc.

In some aspects, the present dehydration systems may be partially or fully integrated with existing systems or other third-party systems, including but not limited to feeding (in/out), grinding, shredding, cutting, pelleting or brick-making systems and/or safety systems. This integration may include one or more of the following: physical devices, power supplies, security, logging and access control devices and data and/or communication equipment.

In other aspects, the present systems provide modularity, which may increase flexibility of placement and orientation of components, increase the degree of component customization, allow for more efficient feeding and servicing of equipment, and increase efficiencies and effectiveness of operation.

In some embodiments, the SSD comprises one or more acceleration channels in which supersonic speed is realized by a vacuum created by one or more turbines; an acceleration channel to transport processed material into a cyclone or several cyclones to separate processed material from moist air.

In some embodiments, air heaters may be attached to the air stream inlet to heat and dry ingoing air.

In some embodiments, condensers may be placed after the air outlet of the cyclone to extract moisture or water from the saturated air for re-application in the irrigation chain.

In some embodiments dust traps may be placed after the air outlet to recover valuable particulate matter and condensers or oil filters may be placed after the air outlet to recover valuable vaporized plant oils, such as terpenes and aromatics.

The operation of SSD, and various features and components of the present disclosure are now described with reference to the Figures.

FIGS. 1A and 1B show the temperature, pressure and velocity of air flowing through an acceleration channel as part of the SSD process. These values are shown as a function of position within the acceleration channel. When air moves with subsonic speed through an acceleration channel, as shown in FIG. 1A, pressure P and temperature T will go down and velocity v will go up before passing the smallest diameter (the "throat" of the acceleration channel). If velocity v does not exceed supersonic speed (Mach 1, or 342 m/s) when passing the throat, all three factors will return to their original levels after the air passed the throat and enters the diverging channel behind the throat.

FIG. 1B shows that, when velocity v does cross the throat at supersonic speed, changes occur in the applicable laws of physics. When passing the throat, velocity v will further and dramatically increase above Mach 1 and pressure p further sinks to almost zero, creating an under-pressure close to vacuum. Temperature T continues to further decrease.

FIG. 2 shows what happens in the acceleration channel when velocity v of air stream 550 hits Mach 1 at the throat. The applicant has used advanced academic software (Ansys 2019-R2) to simulate the development of pressure and velocity when air moves through transonic speed. At point A, an airstream is stabilized, where the velocity v of the air is forced higher at point B until it reaches the throat at point C. Air stream 550 and all material that is in it now pass the throat at transonic speed. Because of the scientifically proven effects of the transition from subsonic to supersonic speed as explained in FIGS. 1A and 1B, velocity v dramatically further increases at point D, while pressure p suddenly drops to near vacuum after passing the throat at point C. After reaching point E, where the original diameter is restored, speed suddenly falls back to subsonic and the vacuum is released. This combination creates strong acoustic shockwaves at line G, because of which the material disintegrates in air stream 550. With the simultaneous temperature drop creating a strong condensation, the contained moisture is absorbed by the air at point F. In this manner, wet material dries and dry air reaches 100% humidity in a fraction of a second.

FIG. 3 shows wet material 501 moving through an embodiment of an acceleration channel 100 according to the present disclosure, from position A to position B to position C. It is generally known that a shockwave S1 is formed at the entrance to the constriction 105 of a venturi, such as acceleration channel 100. On the leading edge of the material 501 at position B, as it is moved through the acceleration channel 100, a bow wave S2 is generated. The forward surface of the material 501 at position C implodes when it hits a standing supersonic shockwave S3 at the end of constriction 105 of the acceleration channel 100. Meanwhile, additional material 501 at position B continues accelerating through recompression shock wave S1. The material 501 at position C collides in one millisecond as it transits the standing shock wave S3. Any liquid held in material 501 instantly becomes vapor. This effectively separates the water content of the wet material 501 from the rest of the material. Tests to dry various materials like corn, hemp, manure, nuts, digestate, garden waste, sewage sludge, greenhouse waste, plastics, leftover meat, dough and eggshells have all shown to be successful.

Knowing the exact moisture content of the material 501, and adjusting air velocity to adjust the bi-directional shock waves S1, S2 and S3 and "dwell time" (namely, the time required or the material 501 to enter/exit the constriction 105) can affect the final moisture content of the material 501 leaving the acceleration channel 100. These parameters also affect the velocity at which the material 501 exits the constriction 100b. Ideally, the exit must happen at low velocity, which results in near-instantaneous deceleration from supersonic speed to a low speed air flow at the exit. This deceleration occurs in approximately one thousandth of one second (one millisecond). The result is that the moisture in material 501 instantaneously turns to vapor.

The moisture content of the material 501 is primarily dependent on what the material is. For example, corn contains 14-16% water, whereas pre-dried pig manure still contains 60-70% water. Therefore, drying manure may require adjustments to the air velocity so as to maximize the drying effect described above. Manure may also from a "second run" through the SSD system, wherein the dried material is sent through the SSD system again to achieve further moisture removal.

Another relevant variable is the humidity of the surrounding air. If it is very humid, the incoming air already contains a high percentage of moisture and therefore cannot absorb the same amount of moisture from the material as when the ambient air is dry. Therefore, System 1 from FIG. 4 can include an air heater (not shown) in front of opening 104 of acceleration channel 100 to dry the incoming air stream before it is used in the drying process.

FIG. 4 shows a schematic view of acceleration channel 100, in accordance with an embodiment of the disclosure. The acceleration channel comprises a cylinder 100*a* having a circular cross-section whose diameter varies along its length. Cylinder 100*a* has an opening 104 for allowing an air stream to enter, and an exit 110 for allowing said air stream to exit the cylinder 100*a*. Since an air stream is intended to move through cylinder 100*a* from its opening 104 to its exit 110, cylinder 100*a* can be said to have an "upstream end" at its opening 104, and a "downstream end" at its exit 110. Cylinder 100*a* can be made of any material of suitable strength to withstand the forces arising through operation of the SSD, for example, polypropylene, reinforced polyester, carbon fiber, stainless steel, or a combination of these materials. In the illustrated embodiment, cylinder 100*a* is a stainless steel pipe having 4 mm thick walls.

Acceleration channel 100 comprises a constriction 100*b*, which is a segment of acceleration channel 100 along which the diameter of the acceleration channel 100 decreases, and then increases back to its original value. The constriction 100*b* comprises: (a) an inclination section 105, along which the diameter of the channel 100 decreases; (b) a throat 106 immediately downstream from inclination section 105, the throat 106 being the point where the diameter of the channel 100 is at its lowest; and (c) a widening section 107 immediately downstream from throat 106, along which the diameter of the channel 100 increases once again. The inner surface of cylinder 100*a* at the junctions between inclination section 105, throat 106 and widening section 107 may be sharp edged or may be rounded off.

In the illustrated embodiment, constriction 100*b* is formed using a polypropylene form, inserted into cylinder 100*a*, and having the specific geometry required to form the constriction 100*b* as described above. It will be understood, however, that constriction 100*b* could also be formed integrally with cylinder 100*a*. In other words, cylinder 100*a* can have interior walls dimensioned so as to form the constriction 100*b* described above.

Acceleration channel 100 also comprises an air pressure sensor 109 mounted downstream from the throat 106. Air pressure sensor 109 is used in the measurement of the velocity of the airstream through the acceleration channel 100, in the manner described in detail below. Air pressure sensor 109 can be any device widely known and available that is capable of obtaining a measurement of air pressure. Air pressure sensor 109 can be mounted to acceleration channel 100 in any manner suitable to allow for the measurement of air pressure within the channel 100 downstream from the throat 106.

Although the SSD process can be achieved using any sort of acceleration channel having a constriction, also known as a venturi tube, the particular dimensions of the acceleration channel will affect the velocity at which air moves through the channel. Accordingly, the geometry of the acceleration channel can be designed to provide the required air velocity (namely, transonic speed or better at the throat of the constriction) using a relatively low input air velocity.

By way of example, acceleration channel 100 can have the following dimensions:

- an interior diameter of 160 mm at all points outside the constriction 100*b*;
- a length from opening 104 to the beginning of the constriction 100*b* of at least 400 mm;
- an inclination section 105 having a length from its beginning to its end at throat 106 of between 100 mm and 400 mm;
- a widening section 107 having a length from its beginning at throat 106 to its end at exit 110 of between 60 and 120 mm; and
- a diameter of the channel 100 at throat 106 that is between 2.5 times smaller and 10 times smaller than the interior diameter of the acceleration channel 100, depending on the type and design of the turbine moving air through the acceleration channel 100.

Dimensions within the ranges outlined above have been observed to provide the air velocity required for the SSD process (i.e., an air velocity at or above the speed of sound at the throat 106) and successfully dry and disinfect materials. The dimensions of the acceleration channel 100 can be further designed such that air velocities at or above the speed of sound at the throat 106 can be achieved as efficiently as possible, namely, with the lowest possible input air velocity. For example, adjustments to the ratio of the throat diameter to the acceleration channel interior diameter can change the airstream velocity through the throat 106, as well as the input airstream velocity required to achieve supersonic airstream velocity through the throat 106.

The design of the dimensions of acceleration channel 100 can also provide other positive effects. For example, providing at least 400 mm from the opening 104 to the beginning of inclination section 105 allows the air stream entering the opening 104 to stabilize before entering the constriction 100b. As another example, the shorter the widening section 107 is made relative to the inclination section 105, the faster the deceleration of the air stream and material will be, making the drying and disinfecting properties of the SSD process more effective.

It is apparent from the foregoing that the SSD process requires that air stream velocity through the throat 106 be at least the speed of sound (342 m/s), or higher. While air stream velocity is commonly measured using pitot tubes, pitot tubes are not suitable for use in turbulent, supersonic environments such as that which exists in the vicinity of the throat 106 when an airstream is moving through channel 100 at high velocity. The velocity of the airstream can instead be measured indirectly by measuring air pressure immediately downstream from the throat 106, using air pressure sensor 109. Using the measured air pressure in this region in combination with known characteristics of the turbine used to generate the airstream through the channel 100 (described in greater detail below), the airstream velocity can be calculated.

FIG. 5 is a graphical representation of the basic air pressure drop over the entire SSD system 1 (shown in FIGS. 7 and 8 and described in greater detail below) after throat 106. Delta $p_v$ 001 is the pressure drop measured by sensor 109, after the throat 106. Delta $p_t$ 002 is the pressure drop over conduit 300 (shown in FIGS. 7 and 8 and described in greater detail below), and delta $p_c$ 003 is the pressure drop over cyclone 400 (shown in FIGS. 7 and 8 and described in greater detail below). In the illustrated embodiment, delta $p_t$ 002 and delta $p_c$ 003 are not measured. Rather, industry best estimates of fixed pressure drops 1000 Pa are used. It will be understood that, for more accurate measurement of airstream velocity through the throat 106, additional air pressure sensors could be added to measure delta $p_t$ 002 and delta $p_c$ 003 directly. Accordingly, it can be seen that the total pressure drop over the entire system is the sum of delta $p_v$ 001, delta $p_t$ 002 and delta $p_c$ 003.

FIG. 6 shows certain specific characteristics of an embodiment of turbine 200 used to create the air stream through channel 100, as described in greater detail below. In particular, FIG. 6 shows both the under pressure generated by the turbine and the power consumed by the turbine's motor, as a function of air volume moved by the turbine per second. Curve 011*a* shows the relation between negative pressure generated by the turbine, and the volume of air moved though the turbine. Curve 011*b* shows the relation between turbine motor power and the volume of air moved through the turbine. Such characteristics are commonly available from manufacturers of turbines.

The calculation of air stream velocity at throat 106 will be shown by way of example. For the purpose of this example, it will be assumed that SSD system 1 has been operated having an observed total air pressure drop (that is, the sum of delta $p_v$ 001, delta $p_t$ 002, and delta $p_c$ 003) of 29,800 Pa, or 298 millibar). This represents a measured pressure drop delta $p_v$ 001 of 27,800 Pa, and best estimate values of 1000 Pa for each of delta $p_t$ 002, and delta $p_c$ 003.

FIG. 6 shows that, at this under-pressure, the turbine processes 1.5 cubic meter of air per second, and uses approximate 78 kW of power. Knowing the volume of air moving through the system per second, as well as the diameter of the throat 106, the airstream velocity through the throat 106 can be calculated. Using a throat having a diameter of 70 mm, the total area of the throat can be calculated as $$\pi * \left(\frac{d}{2}\right)^2,$$

which equals 0.0038 $m^2$ in this case. Airstream velocity can therefore be calculated as 1.5 $m^3$/s÷0.0038 $m^2$=390 m/s. This airstream velocity is sufficiently above the speed of sound for the SSD process to function.

FIG. 7 shows an SSD system 1 that uses acceleration channel 100 for drying and disinfecting material using the SSD process. SSD system 1 has a collector frame 101 attached to the acceleration channel 100 to allow input of material to be dried and disinfected from larger collector entrance 102 into acceleration channel 100 via material entrance 103. Collector 101 can have an integrated shredder (not shown) for reducing the particulate size of incoming material to be dried and disinfected.

Acceleration channel 100 comprises entrance 104 adapted to allow air to be drawn into channel 100 during operation. The particular shape of entrance 104 shown in FIG. 7 is not essential but enhances the ability of air to be sucked into acceleration channel 100.

At exit 110 of acceleration channel 100, the channel 100 is connected to intake 201 of turbine 200, allowing air passing through the channel to enter the turbine 200. Turbine 200 comprises rotor blades 203 on axis 202. Turbine 200 can be driven by any kind of motor, although electrical motors are preferred. Turbine 200 has outlet 204 connected to tube system 300, allowing an air entering the turbine 200 from the acceleration channel 100 to continue onward to tube system 300. Turbine 200 can be any commercially available turbine capable of producing air pressures and air flow sufficient to produce air velocity at or in excess of the speed of sound at the throat 106 of acceleration channel 100. A turbine capable of creating under pressure at its intake in the range of −290 millibar to −390 millibar, and air flow capacity of 1.5 $m^3$ per second to 1.66 $m^3$ per second, has been observed to be effective in generating the required airstream velocity through acceleration channel 100.

Tube system 300 comprises tube 301 and exit 302 creating a path for airflow from the turbine outlet 204 to cyclone 400. Tube 301 and exit 302 can have cylindrical, elliptical, or rectangular cross sections, which may also vary along the length of tube system 300. Exit 302 of tube system 300 is connected the top side of circular cyclone 400, where the entrance is aligned on a tangent to the circular cross-section of the hull 401 of cyclone 400. An airstream and materials entering cyclone 400 via the entrance is directed on a tornado-like helical trajectory within the hull 401. Heavier particles of material within the helically moving airstream, such as dried and disinfected material, will move downward in the hull 401, where they will collect at exit 403 and can be recovered from the cyclone 400 through rotating airlock 404. Lighter materials in the helically moving airstream, such as the moisture laden air received from the acceleration channel 100 and turbine 200, can exit the cyclone 400 through opening 402.

Cyclone 400 can be dimensioned to filter out particles above any specified diameter. It is generally known that the dimensions of cyclones are based on the level of desired separation of dust or solid material from air. The dimensions of cyclone 400 can therefore be selected as appropriate for the given application.

Figure 1A:
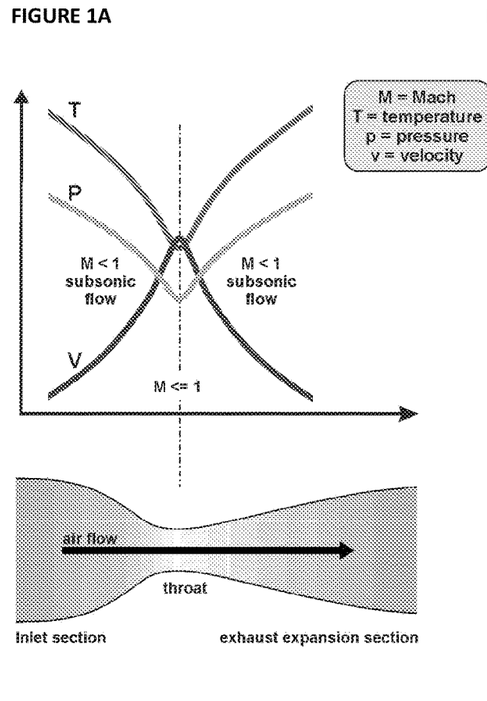
Figure 1B:
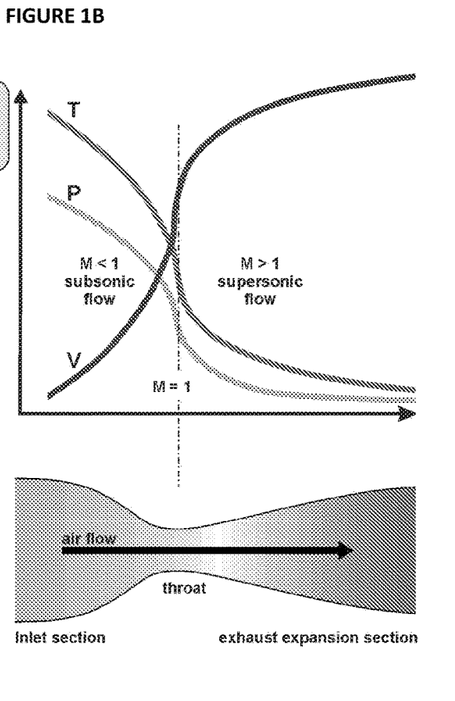
Figure 2:
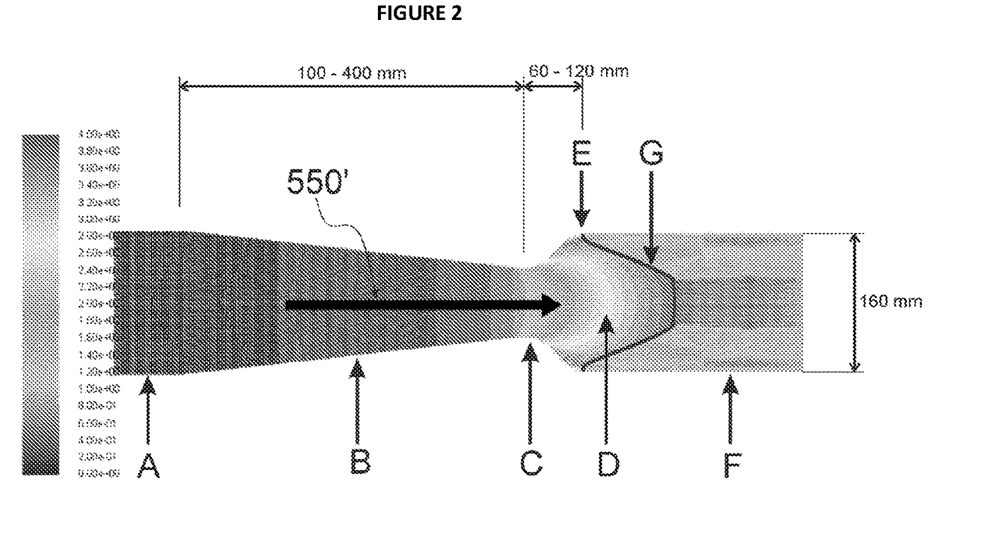
Figure 3:
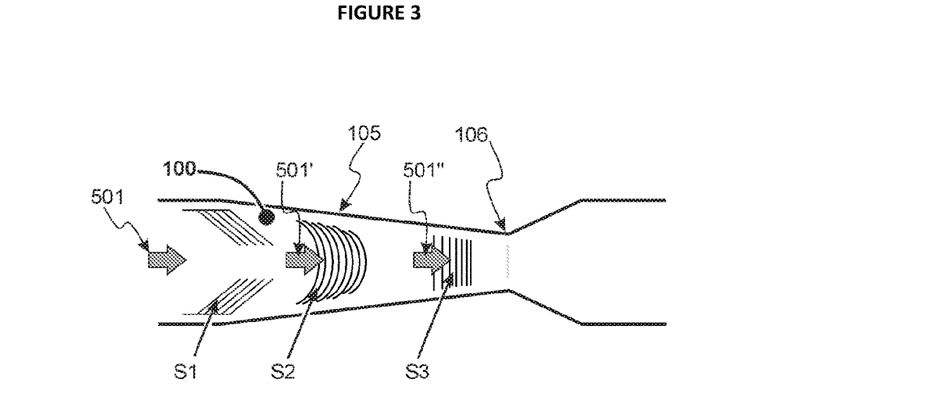
Figure 4:
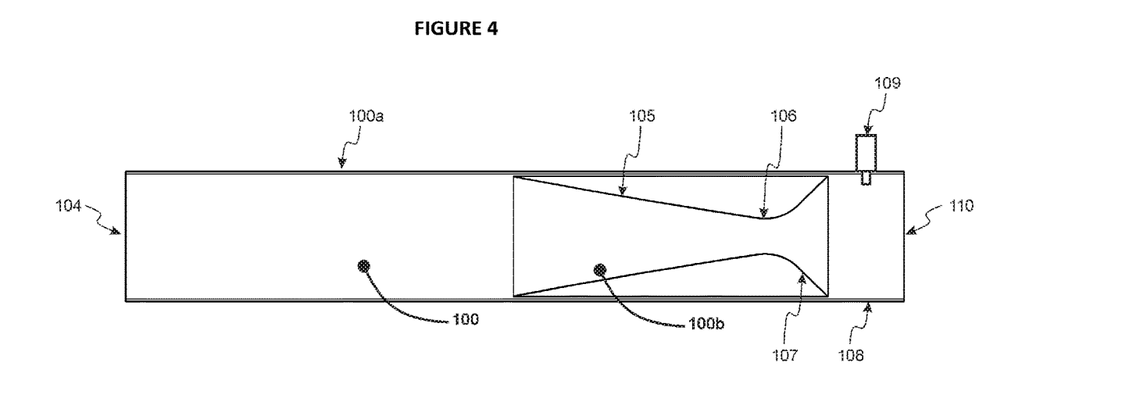
Figure 5:
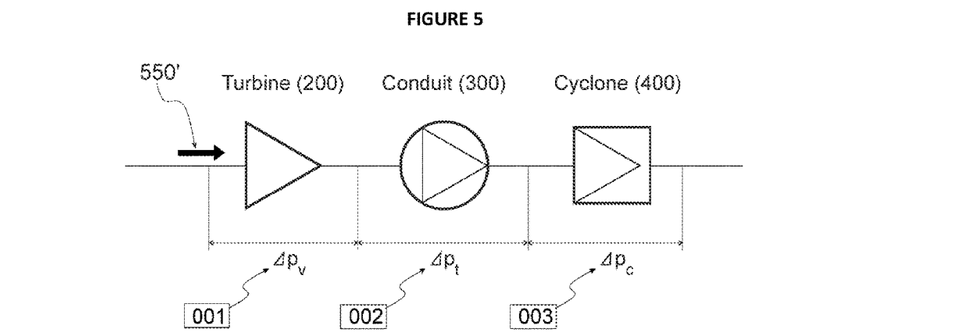
Figure 6:
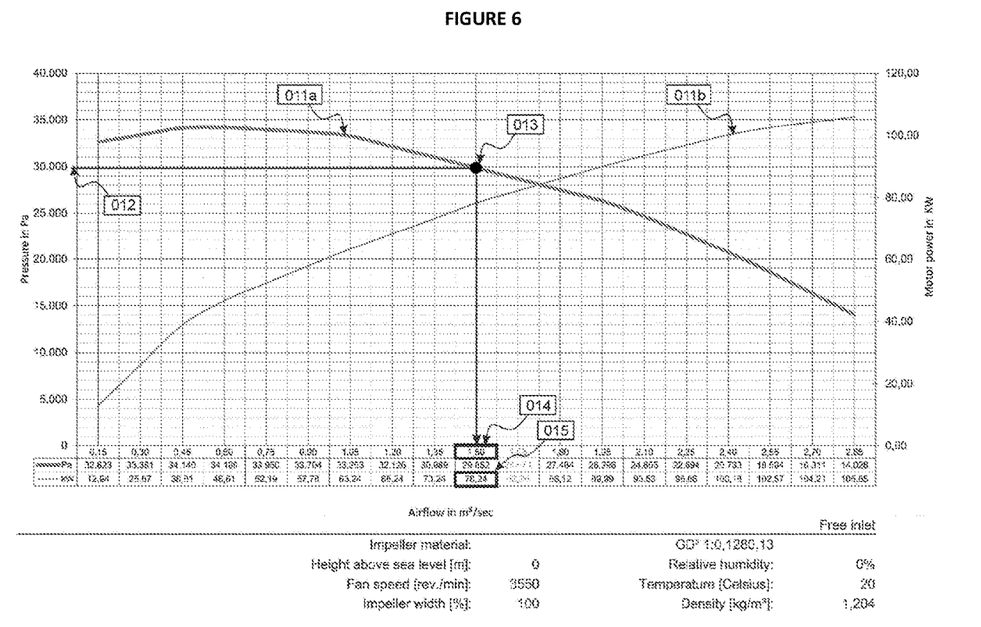
Figure 7:
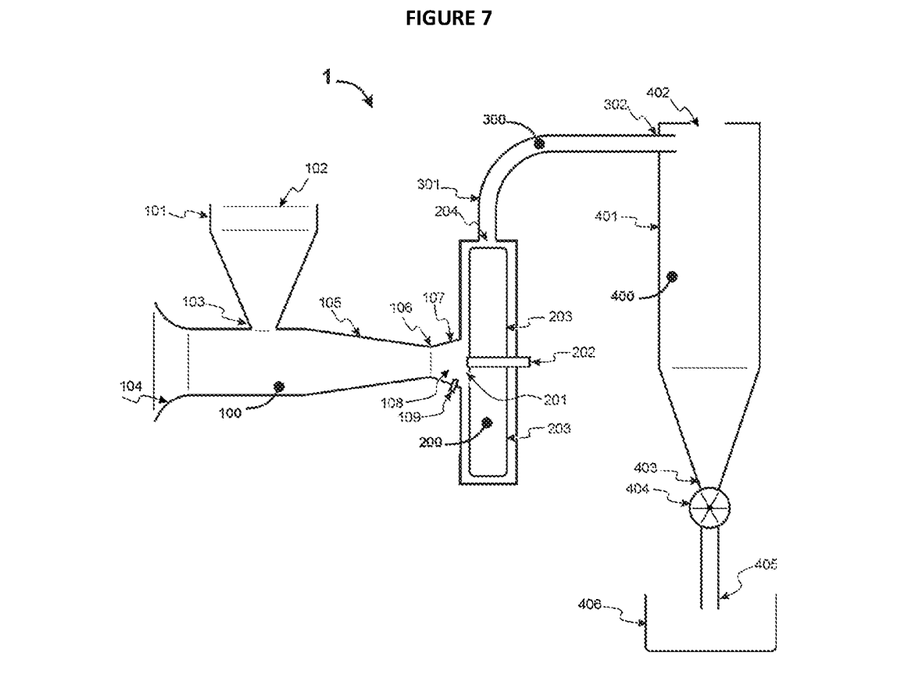
Figure 8:
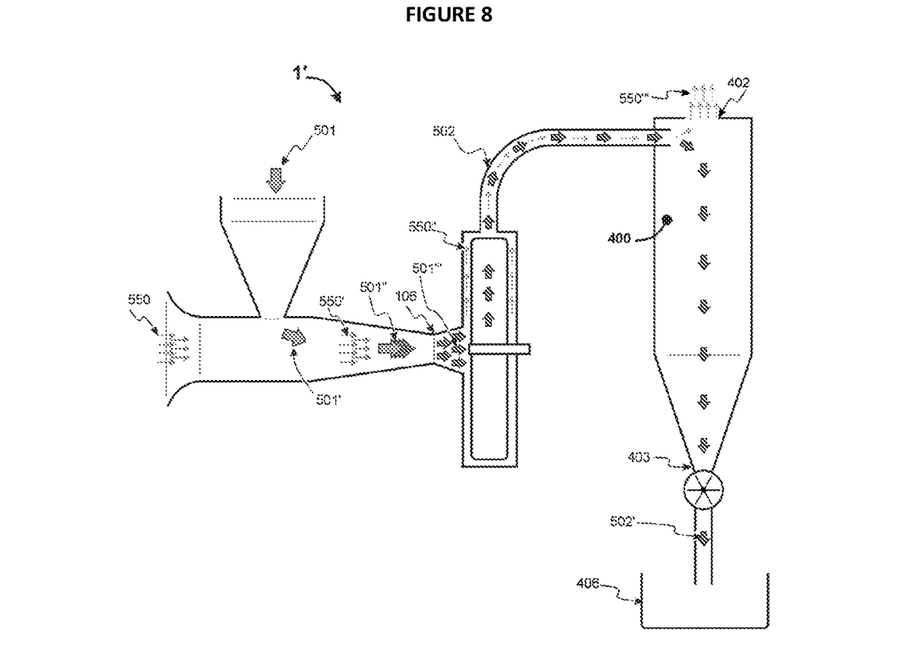
Figure 9:
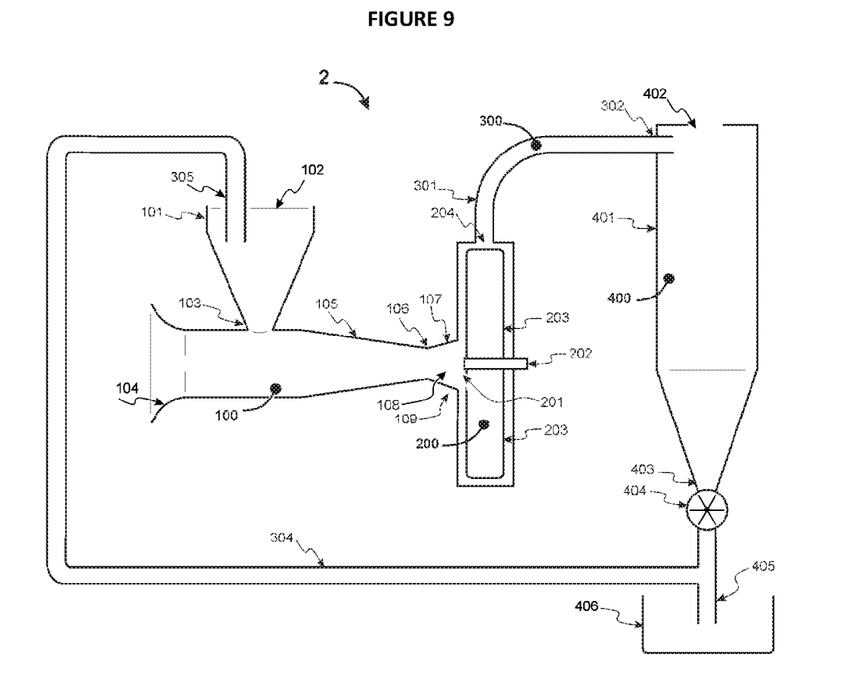
Figure 10:
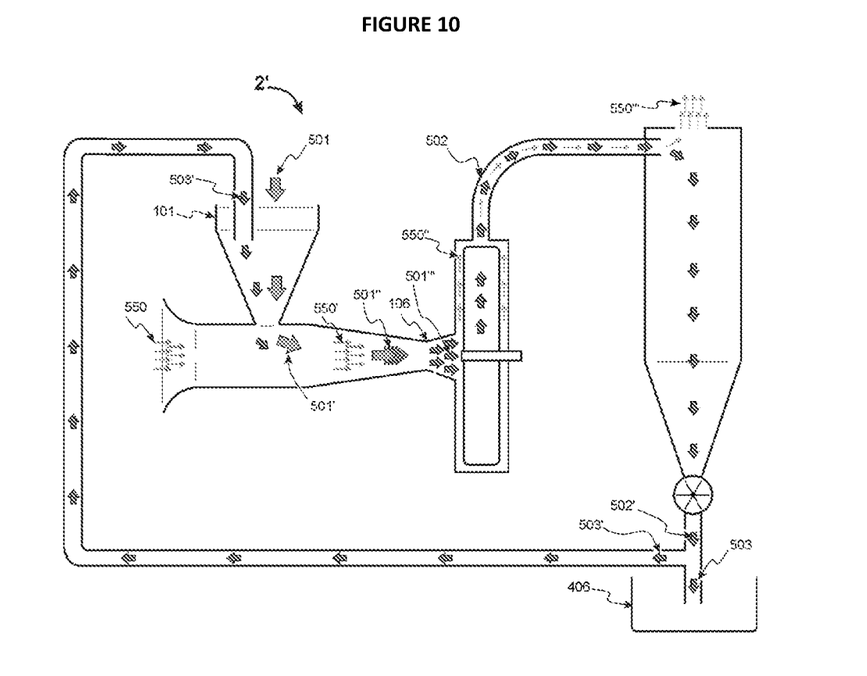
Figure 11:
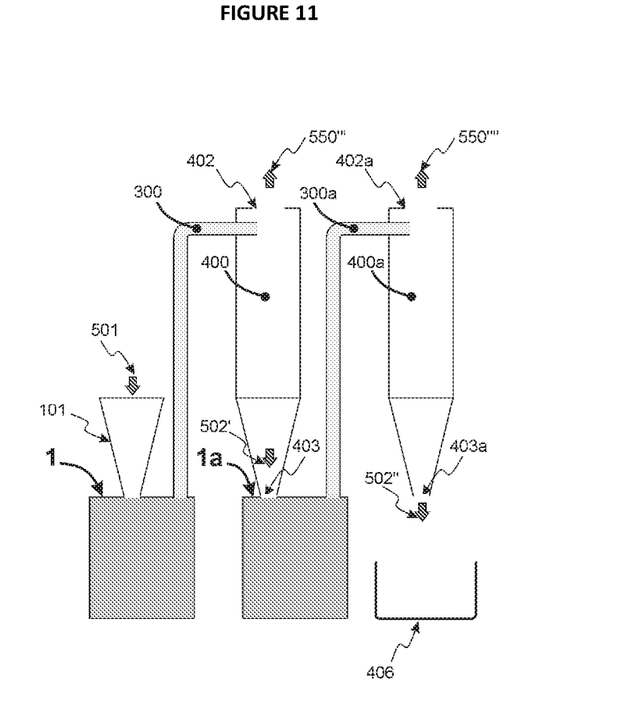
Figure 12:
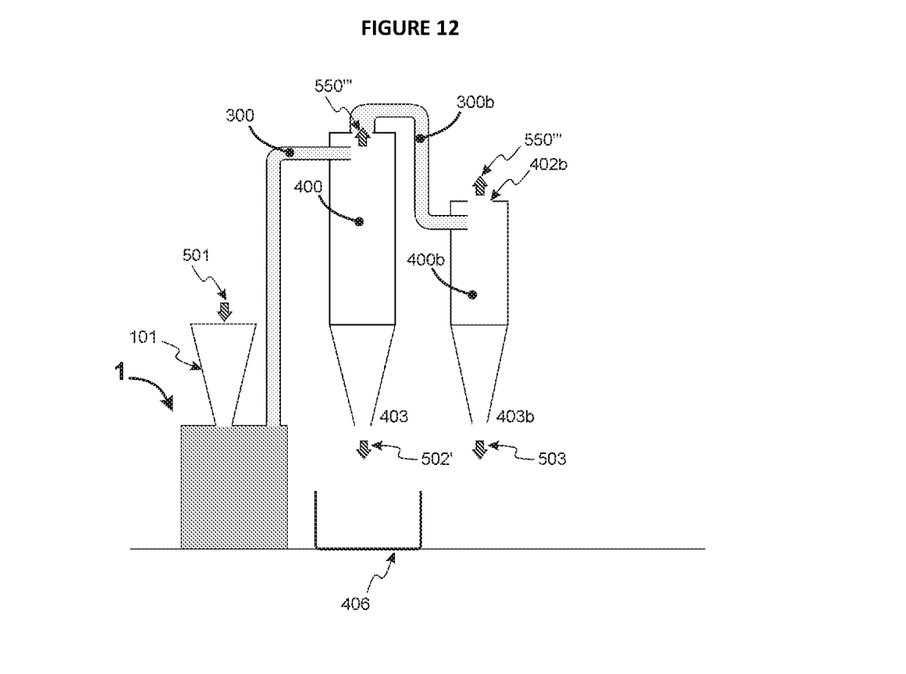
Figure 13:
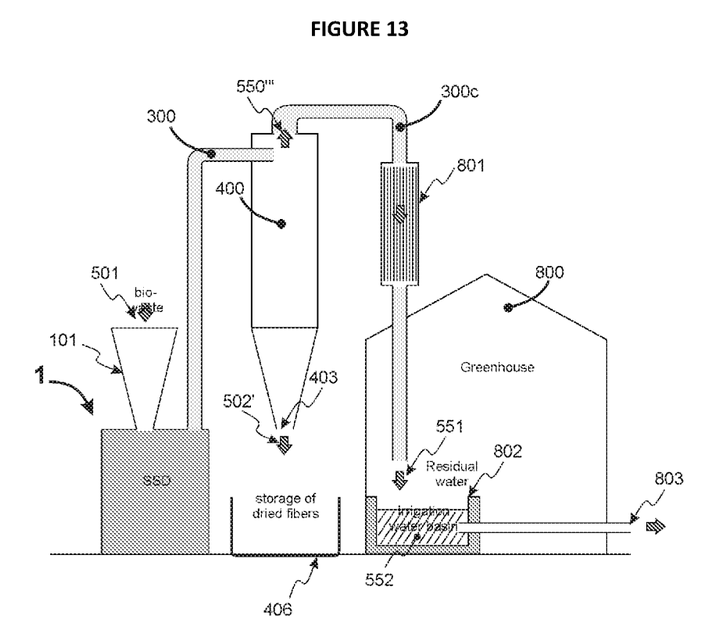

FIG. 8 shows the flow of air and material to be dried and disinfected through the SSD system 1. Turbine 200 is operated at a power level and under pressure value sufficient to produce an airstream velocity through throat 106 that is equal to or greater than the speed of sound. The airstream velocity through throat 106 can be verified using pressure measurements taken downstream from throat 106, in the manner described above.

When turbine 200 is operated as described above, dry air 550 is pulled into Acceleration Channel 100 through entrance 104. Material to be dried and disinfected 501 is added through entrance 102 and falls into the airstream 550. Material 501 can be added through entrance 102 via an automated conveyor system (not shown) that drops material 501 through entrance 102. The operation of this conveyor system can be triggered by the airstream velocity measurement taken indirectly via the air pressure measurement recorded by sensor 109. In particular, once the pressure measured by sensor 109 indicates that airstream velocity through the throat 106 is at the speed of sound or greater, the conveyor system can be activated. This activation can be achieved automatically, by way of control software interconnecting sensor 109 and the conveyor system.

Material 501 and airstream 550 are accelerated towards the speed of sound, moving downstream through cylinder 100*a* and inclination section 105 towards the throat 106. If the distance from opening 104 to the beginning of the constriction 100*b* is sufficient to allow the airstream 550 to stabilize before it enters the constriction 100*b* (400 mm in the illustrated embodiment), material 501 will be flowing smoothly down the middle of cylinder 100*a*, and not interacting with the side walls of cylinder 100*a* by the time the material enters the constriction 100*b*.

As airstream 550 and material 501 transit the throat 106, they accelerate past the speed of sound. Material 501 is subjected to the acceleration and acoustic shock waves described above, the result being that material 501 is disintegrated, moisture comes out of material 501, and the airstream 550 reaches 100% humidity in a fraction of a second.

Disintegrated material 501 and humid airstream 550 exit the acceleration channel 100 and move through turbine 200 and tube system 300 to reach cyclone 400. Material 501 and airstream 550 then begin moving in a helical trajectory within hull 401 of cyclone 400. Disintegrated, dried and disinfected material 501 falls downward to exit 403 where it can be retrieved. In the embodiments shown in FIGS. 7 and 8, rotating airlock 404 can selectively seal off exit 403 or permit material 501 to exit the cyclone 400. Bin 406 can be provided to collect the disintegrated, dried, and disinfected material 501.

FIGS. 9 and 10 show another embodiment of the SSD system 2. SSD system 2 is substantially the same as SSD system 1, but with the addition of a loop-back channel 304. Loop-back channel 304 can be a conveyor belt, or any other suitable means for transporting dried and disinfected material 501 back to opening 102 for a “second run” through the SSD system, where it can be further dried and disinfected.

FIG. 11 shows a further embodiment of the present disclosure, wherein two or more SSD systems 1 can be arranged in series. Exhaust moisture and air 550 leaves cyclone 400 of SSD system 1 on exit 402, and dried, disinfected material 501 leaves cyclone 400 at exit 403. Upon exit, dried and disinfected material 501 is directly fed into another SSD system 1, for further drying and disinfection. It will be apparent that as many SSD systems 1 as may be needed can be arranged in series in this manner.

FIG. 12 shows a schematic setup of a basic SSD system with two cyclones in cascade, where, after the first separation of solid product from moist air, the second cyclone can separate finer particles which were not separated by the first cyclone.

FIG. 12 shows another embodiment of the present disclosure, where a SSD system 1 is provided with two cascaded cyclones 400 and 400*b*. Exhaust moist air 550 moves through conduit 300*b* into cyclone 400*b*, where finer particles 503 leave at exit 403*b*, and moist air 550 leaves at exhaust 402*b*. The dimensioning of cyclone 4*b* is tailored towards the mesh size of leftover particles in exhaust moist air 550', which depends on the material being processed.

FIG. 13 shows a further embodiment of the present disclosure wherein residual water collected from bio waste that has been dried (for example, tomato plants after tomatoes are harvested) is directly added to an irrigation water basin in or outside the greenhouse after being processed by SSD.

FIG. 13 shows an SSD system 1 where solid and partly dried material leaves cyclone 400 at exit 403 and can be collected in a bin 406.

FIG. 13 also shows exhaust moisture and air 550 leaving SSD system 1 through tube system 300*c*. The moisture contained in air 550 can be water or other liquid extracted from the material 501 by way of the SSD process. Such other liquids can include hemp oils or other oils, depending on the type of material 501 being dried. Air stream 550 containing the moisture extracted from material 501 can be fed into moisture collector 801, for the purpose of recovering the moisture. Moisture collector 801 can be any of a number of known technologies for extracting liquid water or other liquids from humid, moisture-laden air. In the illustrated embodiment, moisture collector 801 is a condenser for extracting liquid water from humid air, and water droplets 551 collected from the condenser are deposited in tank 802 to be transported through channel 803 as irrigation water. In other embodiments, moisture collector 801 can be an oil filter, for filtering and collecting oil particles released into air stream 550 by the SSD process. In other embodiments, both a condenser and an oil filter can be used.

FIG. 14 shows a another embodiment of the present disclosure wherein acceleration channel 100 has no collector, and material 501 is sucked into opening 104 of acceleration channel 100 directly by the airstream created by turbine 200 from e.g. an external collector belt or other mechanical transportation or feeding system (not shown).

From the foregoing, numerous advantages of the SSD process will be apparent. The SSD can be used to dry bulk material, reducing its weight and volume and thus making it easier and less expensive to transport. The SSD accomplishes this while consuming approximately 100 kW of power to process approximately 2 metric tons of material per hour. This is less than 25% of the power consumption required to operate traditional fossil fuel-based systems for drying waste. As well, the carbon footprint of the SSD system is much smaller than that of traditional heat-based drying systems, since SSD uses only an electric motor. Furthermore, since an SSD system can operate with minimal maintenance and supervision, the operation cost of an SSD system will be lower than that of conventional drying systems.

As well, the SSD system can accomplish the drying and disinfection of bulk organic material without using any heat, and without the addition of any viscosity modifying agent.

Accordingly, the present structures and systems may provide for supersonic dehydration systems and structures, improved customization of types and positioning of various equipment, and improved ease of access to equipment for maintenance.

The structure, features, accessories, and alternatives of specific embodiments described herein and shown in the Figures are intended to apply generally to all the teachings of the present disclosure, including to all the embodiments described and illustrated herein, insofar as they are compatible. In other words, the structure, features, accessories, and alternatives of a specific embodiment are not intended to be limited to only that specific embodiment, unless so indicated.

Furthermore, additional features and advantages of the present disclosure will be appreciated by those skilled in the art. By way of example, tube system 300 that carries humid airstream and dried material to cyclone 400 and connect to two or more cyclones 400, as permitted by the physical space available on site, to increase the capacity of the SSD system. As well, cyclone 400 can contain dust filters, for example, HEPA filters (not shown) to capture very fine particles of dried, disinfected material.

In addition, the embodiments described herein are examples of structures, systems or methods having elements corresponding to elements of the techniques of this application. This written description may enable those skilled in the art to make and use embodiments having alternative elements that likewise correspond to the elements of the techniques of this application. The intended scope of the techniques of this application thus includes other structures, systems or methods that do not differ from the techniques of this application as described herein, and further includes other structures, systems or methods with insubstantial differences from the techniques of this application as described herein.

Moreover, the previous detailed description is provided to enable any person skilled in the art to make or use the present invention. Various modifications to those embodiments will be readily apparent to those skilled in the art, and the generic principles defined herein may be applied to other embodiments without departing from the spirit or scope of the invention described herein. Thus, the present invention is not intended to be limited to the embodiments shown herein, but is to be accorded the full scope consistent with the claims, wherein reference to an element in the singular, such as by use of the article "a" or "an" is not intended to mean "one and only one" unless specifically so stated, but rather "one or more". All structural and functional equivalents to the elements of the various embodiments described throughout the disclosure that are known or later come to be known to those of ordinary skill in the art are intended to be encompassed by the elements of the claims. Moreover, nothing disclosed herein is intended to be dedicated to the public regardless of whether such disclosure is explicitly recited in the claims.

What is claimed is:

1. An apparatus for dehydrating or disinfecting material, the apparatus comprising:
   an acceleration channel having an inlet for receiving an air stream and material to be dehydrated, an outlet for discharging said air stream and dehydrated, disinfected material, and a constriction positioned between the inlet and the outlet; an air mover in communication with the acceleration channel for moving an air stream and material to be dehydrated through the acceleration channel such that a velocity of the air stream and material moving through the constriction is equal to or greater than a speed of sound; and
   a cyclone in communication with the outlet of the acceleration channel for receiving said discharged air stream and dehydrated, disinfected material, and separating said dehydrated, disinfected material from said air stream.

2. The apparatus of claim 1, wherein the constriction is positioned at least 400 millimeters from the inlet of the acceleration channel.

3. The apparatus of claim 1, wherein the constriction comprises:
   a first length forming an inclination section in which a diameter of the acceleration channel decreases;
   a second length forming a widening section in which the diameter of the acceleration channel increases; and
   a throat, located at a point between the inclination section and the widening section where the diameter of the acceleration channel is smallest.

4. The apparatus of claim 3, wherein the length of the inclination section is within a range of 100 millimeters and 400 millimeters.

5. The apparatus of claim 3, wherein the length of the widening section is within a range of 60 millimeters and 120 millimeters.

6. The apparatus of claim 3, wherein a ratio of the diameter of the acceleration channel at the throat, to a maximum diameter of the acceleration channel is within a range of 1:2.5 to 1:10.

7. The apparatus of claim 1, wherein the acceleration channel has an interior diameter of about 160 millimeters at all points outside the constriction.

8. The apparatus of claim 1, wherein an intake of the air mover is in communication with the outlet of the acceleration channel, and the cyclone is in communication with an outlet of the air mover.

9. The apparatus of claim 1, wherein the air mover is a turbine capable of generating under pressure in a range of −290 millibar to −390 millibar, and airflow capacity in a range of 1.5 $m^3$ per second to 1.66 $m^3$ per second.

10. The apparatus of claim 1, further comprising an air pressure sensor in communication with the acceleration channel, for measuring air pressure within the channel.

* * * * *